(12) United States Patent
Vemishetti et al.

(10) Patent No.: US 10,154,948 B2
(45) Date of Patent: Dec. 18, 2018

(54) ORAL COMPOSITIONS CONTAINING ZINC, STANNOUS AND FLUORIDE ION SOURCES

(71) Applicant: COLGATE-PALMOLIVE COMPANY, New York, NY (US)

(72) Inventors: Kavita Vemishetti, Monmouth Junction, NJ (US); Linh Fruge, Hillsborough, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/319,636

(22) PCT Filed: Jun. 20, 2014

(86) PCT No.: PCT/US2014/043427
§ 371 (c)(1),
(2) Date: Dec. 16, 2016

(87) PCT Pub. No.: WO2015/195140
PCT Pub. Date: Dec. 23, 2015

(65) Prior Publication Data
US 2017/0319447 A1    Nov. 9, 2017

(51) Int. Cl.
| | | |
|---|---|---|
| A61K 8/27 | (2006.01) | |
| A61K 8/365 | (2006.01) | |
| A61K 8/24 | (2006.01) | |
| A61K 8/21 | (2006.01) | |
| A61Q 11/00 | (2006.01) | |
| A61K 8/19 | (2006.01) | |

(52) U.S. Cl.
CPC .............. *A61K 8/27* (2013.01); *A61K 8/19* (2013.01); *A61K 8/21* (2013.01); *A61K 8/24* (2013.01); *A61K 8/365* (2013.01); *A61Q 11/00* (2013.01)

(58) Field of Classification Search
CPC .............. A61K 8/21; A61K 8/31; A61K 8/66
USPC ........................................ 424/49, 50
See application file for complete search history.

(56) References Cited

U.S. PATENT DOCUMENTS

| | | |
|---|---|---|
| 2,946,725 A | 7/1960 | Norris et al. |
| 3,070,510 A | 12/1962 | Cooley et al. |
| 3,538,230 A | 11/1970 | Pader et al. |
| 3,678,154 A | 7/1972 | Widder et al. |
| 3,862,307 A | 1/1975 | Di Giulio |
| 3,959,458 A | 5/1976 | Agricola et al. |
| 3,966,863 A | 6/1976 | Forward et al. |
| 3,980,767 A | 9/1976 | Chown et al. |
| 4,051,234 A | 9/1977 | Gieske et al. |
| 4,206,215 A | 6/1980 | Bailey |
| 4,328,205 A | 5/1982 | Taylor |
| 4,340,583 A | 7/1982 | Wason |
| 4,358,437 A | 11/1982 | Duke |
| 4,627,977 A | 12/1986 | Gaffar et al. |
| 4,894,220 A | 1/1990 | Nabi et al. |
| 5,004,597 A | 4/1991 | Majeti et al. |
| 5,015,466 A | 5/1991 | Parran, Jr. et al. |
| 5,047,490 A | 9/1991 | Pehlah et al. |
| 5,578,293 A | 11/1996 | Prencipe et al. |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,716,601 A | 2/1998 | Rice |
| 5,718,885 A | 2/1998 | Gingold et al. |
| 5,759,523 A | 6/1998 | Hughes et al. |
| 6,019,962 A | 2/2000 | Rabe et al. |
| 6,024,891 A | 2/2000 | Hughes |
| 6,123,950 A | 9/2000 | Hughes |
| 6,139,823 A | 10/2000 | Drechsler et al. |
| 6,162,418 A | 12/2000 | Randive et al. |
| 6,187,293 B1 | 2/2001 | Ballard |
| 6,685,920 B2 | 2/2004 | Baig et al. |
| 8,906,347 B2 | 12/2014 | Strand et al. |
| 2007/0053849 A1* | 3/2007 | Doyle .............. A61K 8/02 424/50 |
| 2012/0207686 A1* | 8/2012 | Fruge .............. A61K 8/20 424/52 |

FOREIGN PATENT DOCUMENTS

| | | |
|---|---|---|
| WO | 1994/014406 | 7/1994 |
| WO | 2011/016982 | 2/2011 |
| WO | WO 2011/053291 | 5/2011 |

OTHER PUBLICATIONS

Rautemaa et al., "Oral infections and systemic disease—an emerging problem in medicine." Clin Micorbiol Infect 2007; 13: 1041-1047. (Year: 2007).*

International Search Report and Written Opinion for corresponding PCT/US2014/043427 dated Feb. 18, 2015.

* cited by examiner

*Primary Examiner* — Walter E Webb

(57) ABSTRACT

An oral care composition containing a source of stannous ions, a source of fluoride ions and an insoluble source of zinc ions, such as zinc oxide. The composition contains an amount of citric acid sufficient to increase the level of soluble zinc ions.

19 Claims, No Drawings

ORAL COMPOSITIONS CONTAINING ZINC, STANNOUS AND FLUORIDE ION SOURCES

CROSS-REFERENCE TO RELATED PATENT APPLICATIONS

The present application is a U.S. national stage application under 35 U.S.C. § 371 of PCT Application No. PCT/US2014/043427 filed Jun. 20, 2014, the entirety of which is incorporated herein by reference.

BACKGROUND

There is a need for agents in oral care products that provide enhanced benefits including antibacterial, anticavity, enamel erosion prevention, breath freshening, and the like. The antibacterial effects of zinc ions, stannous ions and/or fluoride ions in the oral cavity are described in the art and numerous attempts have been made to prepare dentifrice compositions incorporating zinc ions, stannous ions and/or fluoride ions to take advantage of therapeutic benefits such as reduced plaque, gum inflammation, gingivitis, and the like. In particular, soluble zinc salts, such as zinc citrate, have been used in dentifrice compositions.

Insoluble zinc ion sources, such as zinc oxide, have also been disclosed for use in dentifrices, see for example US Patent Application Publication 2012/0207686 ("the '686 publication"). However, use of insoluble zinc salts often is limited by the low levels of zinc ions available for delivery to tooth surfaces, and undesirable consumer astringency when higher levels of zinc are used.

It would be desirable to provide an oral care composition which exhibits even greater efficacy than previously-known compositions in its prevention and/or reduction of biofilm, plaque, oral inflammation, and the like.

BRIEF SUMMARY

The present invention relates to an oral care composition, for example a dentifrice composition, that can effectively combine a stannous ion source, a fluoride ion source, and an insoluble zinc ion source in a low water, preferably single phase, system that has efficacious delivery the ions to the oral cavity. Stannous and zinc ions have been found to help in the reduction/prevention of oral inflammation such as gingivitis and periodontitis, plaque formation, oral biofilm formation, tooth sensitivity, and improved breath benefits.

The present invention concerns an oral care composition comprising:
(a) an orally acceptable carrier;
(b) a source of fluoride ions;
(c) a source of stannous ions;
(d) an insoluble source of zinc ions;
(e) a buffering system comprising citric acid wherein the amount of citric acid is at least 1% by weight of the composition, and
wherein the composition has a total water content of less than 15% by weight.

In another aspect, the embodiments described herein provide a method for the treatment and prevention of bacterial plaque accumulation comprising administering to the oral cavity the dentifrice composition described above.

It should be understood that the detailed description and specific examples, while indicating the preferred embodiment of the invention, are intended for purposes of illustration only and are not intended to limit the scope of the invention.

DETAILED DESCRIPTION

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In this description, unless otherwise stated, the use of the singular also includes the plural. For example, "a stannous ion source" also comprehends the case where more than one stannous ion source is used.

As used herein, the words "preferred" and "preferably" refer to embodiments of the invention that afford certain benefits, under certain circumstances. However, other embodiments also may be preferred, under the same or other circumstances. Furthermore, the recitation of one or more preferred embodiments does not imply that other embodiments are not useful, and is not intended to exclude other embodiments from the scope of the invention.

Insoluble Zinc Ion Source

The insoluble zinc ion source in one embodiment is an insoluble zinc ion salt. As used herein the term "insoluble" means the material or compound has a solubility of less than 0.1 wt. % (based on the weight of the composition) in a 25° C. water solution at pH 7. It also will be understood that at lower or higher pH, the insoluble zinc ion sources may become significantly more soluble. Examples of suitable insoluble zinc ion sources include zinc oxide, zinc phosphate, zinc pyrophosphate, and other zinc compounds. The insoluble zinc ion source preferably is zinc oxide.

In general, the higher the level of solubilized zinc ions available for delivery to oral surfaces, the higher the level of efficacy. The present invention provides for high levels of zinc ions to be present in the composition from the insoluble zinc ion source. Typically, a composition of the invention has greater than 50% soluble zinc ions (e.g. for a composition with 1% by weight (1.0) of an insoluble zinc ion source, the amount of zinc would be greater than 0.5% (0.5) after aging for 13 weeks at 40° C.), in other embodiments greater that 60%, greater than 70%, or greater than 80%, after aging for 13 weeks at 40° C.

The amount of zinc ion source typically will be present in an amount of from 0.1% to 2 wt. %, by weight of the final composition. In one embodiment, the zinc ion source is present in an amount of from 0.5 to 1.5%, or from 0.9% to 1.1%.

Stannous Ion Source

The compositions of the present invention comprise a stannous ion source. The stannous ion source can be a soluble or an insoluble compound of stannous with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous.

Oral compositions containing stannous salts, particularly stannous fluoride and stannous chloride, are described in U.S. Pat. No. 5,004,597. Other descriptions of stannous salt dentifrices are found in U.S. Pat. No. 5,578,293. The preferred stannous salts are stannous fluoride and stannous chloride dihydrate. Other examples of stannous salts include stannous acetate, stannous tartrate and sodium stannous citrate.

In general, the higher the level of solubilized stannous ions available for delivery to oral surfaces, the higher the level of efficacy. The present invention provides for high levels of stannous ions to be present in the composition from the insoluble zinc ion source. Typically, a composition of the invention has greater than 50% soluble stannous ions, in other embodiments greater that 60%, greater than 70%, greater than 80%, or greater than 90% after ageing for 13 weeks at 40° C.

The stannous ion source typically will be present in an amount of from 0.05% to 5%, by weight of the final composition. In one embodiment, the stannous ion source is present in an amount of from 0.1 to 1%, or from 0.35% to 0.55%.

Stannous and zinc ions are derived from the ion source(s) found in the oral care composition in an effective amount. An effective amount is defined as from at least 1000 ppm metal (zinc plus stannous) ion, preferably 2,000 ppm to 15,000 ppm. More preferably, metal ions are present in an amount from 3,000 ppm to 13,000 ppm and even more preferably from 4,000 ppm to 10,000 ppm. This is the total amount of metal ions (stannous and zinc) that is present in the compositions for delivery to the tooth surface.

The combined metal ion sources (stannous and zinc) typically will be present in an amount of from 0.15% to 7%, by weight of the final composition. Preferably, the metal ion sources are present in an amount of from 0.6 to 2.5%, more preferably from 1.25% to 1.65%.

Fluoride Ion Source

The fluoride ion source herein is a fluoride source capable of providing free fluoride ions. Soluble fluoride ion sources include sodium fluoride, stannous fluoride, indium fluoride, zinc fluoride, and sodium monofluorophosphate. Sodium fluoride and stannous fluoride are the preferred soluble fluoride ion sources. U.S. Pat. No. 2,946,725 and U.S. Pat. No. 3,678,154, disclose such fluoride ion sources as well as others.

The fluoride ion source in the present compositions preferably is present as a solid dispersion in the composition during storage, prior to actual brushing usage of the composition by a consumer. The level of water in the present compositions is too low to permit the fluoride source to dissolve in the composition during storage. Thus, interaction between the fluoride ion and other ingredients such the polyphosphate, or silica if present, is minimized during storage, providing a stable composition during storage. When the composition is contacted by saliva and/or water at the time of brushing, the fluoride source preferably will be dispersed and the active ion will be delivered to the oral cavity.

The present compositions may contain a soluble fluoride ion source capable of providing from 50 ppm to 3500 ppm, and preferably from 500 ppm to 3000 ppm of free fluoride ions. To deliver the desired amount of fluoride ions, fluoride ion source may be present in the total oral care composition at an amount of from 0.1% to 5%, in one embodiment from 0.2% to 1%, and even from 0.3% to 0.6%, by weight of the total composition.

Buffering System

The compositions described herein also contain a buffering system comprising citric acid. It has been surprisingly found that an amount of citric acid greater than 0.6%, by weight of the oral care composition will result in substantially more zinc ions and or stannous ions being present in the composition, from the respective zinc and/or stannous ion sources in the composition, when aged at 40° C. for 8 or 13 weeks. In some embodiments the amount of citric acid is 0.5-4 wt. % or 1-3 wt. %, or 1.1-1.5 wt. % or 1.8-2.2 wt. % or 1.3% or 2% by weight of the oral care composition. In one embodiment the buffering system comprises citric acid and sodium citrate, in particular trisodium citrate. Buffering agents, as used herein, refer to agents that can be used to adjust the pH of the compositions to a range of pH 3.0 to pH 10, more typically 6 to 8.

In addition to citric acid, other buffering agents which may optionally be present include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, and pyrophosphate salts. Total amounts of buffering agents typically are from 0.1% to 30%, or from 0.1% to 10%, or from 0.3% to 3%, by weight of the present composition.

Total Water Content

Water employed in the preparation of commercially suitable oral compositions should preferably be of low ion content and free of organic impurities. In the dentifrice composition, water will generally comprise less than 20 wt. %, or less than 15 wt. %, or from less than 15% to greater than 10 wt. %, by weight of the composition herein. The amounts of water include the free water that is added plus that which is introduced with other materials, such as with silica, surfactant solutions, and/or color solutions.

Orally Acceptable Carrier

In certain embodiments, the present invention provides compositions comprising an orally acceptable carrier or vehicle. As used herein, an "orally acceptable carrier" and "orally acceptable vehicle" are used interchangeably, and refer to a material or combination of materials that is safe for use in the present compositions, commensurate with a reasonable benefit/risk ratio, with which the other ingredients may be associated while retaining significant clinical efficacy. Such carrier materials should be selected for compatibility with the other ingredients of the compositions, and preferably do not substantially reduce the efficacy of the other ingredients. Selection of specific carrier components is dependent on the desired product form, including dentifrices, rinses, gels, and paints.

Materials useful in carriers include but are not limited to: adhesion agents, thickening agents, viscosity modifiers, diluents, surfactants, anticalculus agents, abrasives, foam modulators, whitening agents such as peroxides, peroxide activators, peroxide stability agents, pH modifying agents, humectants, mouth feel agents, sweeteners, flavorants, colorants, and combinations thereof.

Adhesion Agents

As used herein, an "adhesion agent" is a material or combination of materials that enhances the retention of an ingredient to an oral cavity surface onto which it is applied. Such adhesion agents include without limitation: adhesives, film forming materials and viscosity enhancers; for example, hydrophilic organic polymers, hydrophobic organic polymers, silicone gums, silicone adhesives, silicas, and combinations thereof. In one embodiment adhesive agent is a methyl vinyl ether/maleic anhydride copolymer having an average molecular weight (M.W.) of 30,000 to 1,000,000, e.g. 300,000 to 800,000. Preparation of the polymethyl vinyl ether-maleic anhydride copolymer is specifically set forth in U.S. Pat. Nos. 5,047,490 and 4,627,977. The polymethyl vinyl ether maleic anhydride copolymer is also commercially available under the trade name Gantrez® AN from ISP (Ashland), Wayne, N.J.

Thickening Agents

The dentifrice compositions of the present invention may incorporate one or more thickening agents which may act as a binder system. The total amount of thickening agent is typically from 0% to 3 wt. %, or from 0.1% to 1.5 wt. %, or from 0.2%-0.5 wt. % by weight of the oral care composition One such thickening agent is polyvinylpyrrolidone (PVP), in particular crosslinked PVP, optionally in combination with a gum such as xanthan gum. Other thickening agents include polysaccharides, carbomers, poloxamers, modified celluloses, e.g., carboxymethyl cellulose (CMC), and mixtures thereof. In some embodiments these thickening agents provide desirable consistency and gellation to the low water oral care composition. It has previously been known that gelling materials that provide desirable rheology with water and humectant provide generally less satisfactory rheology when the water is not present to activate their gellation binding properties. This is believed to be especially true of glycerin humectant. The thickening agent may also comprise additional inorganic thickening agents.

Polysaccharides, including gums, that are suitable for use herein as thickening agents include carageenans, gellan gum, locust bean gum, xanthan gum, and mixtures thereof. Carageenan is a polysaccharide derived from seaweed and has been known for use as a binder or thickener in toothpastes, see, e.g., U.S. Pat. Nos. 6,187,293 B1 and 6,162,418. There are several types of carageenan that may be distinguished by their seaweed source and/or by their degree of and position of sulfation. Suitable for use in the present invention are kappa carageenans, modified kappa carageenans, iota carageenans, modified iota carageenans, and mixtures thereof. Carageenans suitable for use herein include those commercially available from the FMC Company under the series designation "Viscarin," including but not limited to Viscarin TP 329, Viscarin TP 388, and Viscarin TP 389.

Gellan gum is another polysaccharide that is suitable for use herein. It is a polysaccharide aerobically fermented by *pseudomonas elodea*. It can also form an acceptable low water matrix when it is present at a level of from 0.1% to 3%, preferably from 0.4% to 1.8% (w/w).

Locust bean gum and xanthan gum are also suitable polysaccharides for use herein. Locust bean gum or xanthan gum as thickening agents can form a stable and acceptable dentifrice matrix when water level is lower than 10% in the composition.

Poloxamers are also suitable as thickening agents in the low water matrix herein. Poloxamer is a synthetic block copolymer of ethylene oxide and propylene oxide. It is available in several types. Herein, poloxamer 407 is preferable. It can be partly dissolved in water. When temperature is higher than 65° C., it can dissolve in glycerin. POLOXAMER 407® is available, for example, from the BASF CORPORATION, New Jersey, USA.

Carbomers are also suitable as thickening agents in a low water matrix, especially in non-water matrix.

Modified celluloses such as hydroxyethyl cellulose and CMC are also good thickening agents in low water matrix. Since the water level is limited in the present compositions, modified hydroxyethyl cellulose with a hydrophobic chain ($C_{12}$-$C_{20}$) are preferred to increase the solubility and hydration of this thickening agent in other low polar solvents, such as glycerin, propylene glycol and polyethylene glycol (PEG).

The thickening agent may comprise inorganic thickening agents such as colloidal magnesium aluminum silicate or finely divided silica to further improve texture. Additional inorganic thickening agents if present can be used in an amount from 0.1% to 15%, more preferably from 0.1% to 5%, by weight of the oral care composition.

Humectant

The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from 0.1% to 70%, preferably from 1% to 60%, and more preferably from 15% to 55%, by weight of the composition.

The humectant is believed to have a significant impact on the viscosity of the low water matrix. For example, when using polysaccharide as the thickening agent in the composition, the viscosity of the matrix will increase when the level of glycerin or polyethylene glycol increases. On the contrary, the viscosity of matrix will decrease when the level of propylene glycol increases in the composition.

Anticalculus Agents

In various embodiments of the present invention, the oral care composition may comprise an anticalculus (tartar control) agent. Generally, tartar control agents are categorized as being incompatible with some whitening agents, but embodiments of the present invention incorporate tartar control agents and whitening agents in a single phase whitening composition. Suitable anticalculus agents include without limitation phosphates and polyphosphates (for example pyrophosphates and tripolyphosphates), polyaminopropanesulfonic acid (AMPS), hexametaphosphate salts, zinc citrate trihydrate, polypeptides (such as polyaspartic and polyglutamic acids), polyolefin sulfonates, polyolefin phosphates, and diphosphonates (e.g., EHDP; AHP). The oral composition may include a mixture of different anticalculus agents. In one preferred embodiment, tetrasodium pyrophosphate (TSPP), sodium tripolyphosphate (STPP), tetrapotassium pyrophosphate (TKPP), or mixtures thereof are used. The anticalculus agent may comprise 0.1% to 30% or 0.1% to 15%, or 1% to 10%, or 2% to 6%, by weight.

Abrasives

An abrasive polishing material may also be included in the toothpaste compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed in U.S. Pat. No. 3,070,510. Mixtures of abrasives may also be, used. If the dentifrice composition or particular phase comprises a polyphosphate having an average chain length of 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between 0.1 to 30 microns, and preferably from 5 to 15 microns. The abrasive can be precipitated silica or silica gels such as the silica xerogels described in U.S. Pat. No. 3,538,230, and U.S. Pat. No. 3,862,307. Preferred are the silica xerogels marketed under the trade name "SYLOID®" by the W. R. Grace & Company, Davison Chemical Division. Also preferred are the precipitated silica materials such as those marketed by the J. M. Huber Corporation under the trade name, "ZEODENT®", particularly the silica carrying the designation "Zeodent 119." The types of silica dental abrasives useful in the toothpastes of the present invention are described in more detail in U.S. Pat. No. 4,340,583. Silica abrasives are also described in U.S. Pat. Nos. 5,589,160; 5,603,920; 5,651,958; 5,658,553; and 5,716,601. The abrasive in the oral care compositions described herein is generally present at a level of from 6% to 70% by weight of the composition. Preferably, toothpastes contain from 10% to 50% of abrasive, by weight of the composition.

Peroxide Source

The present invention may include a peroxide source in the composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from 0.01% to 10%, preferably from 0.1% to 5%, more preferably from 0.2% to 3%, and most preferably from 0.3% to 0.8% of a peroxide source, by weight of the dentifrice composition.

Alkali Metal Bicarbonate Salt

The compositions also may include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from 0.5% to 50%, preferably from 0.5% to 30%, more preferably from 2% to 20%, and most preferably from 5% to 18% of an alkali metal bicarbonate salt, by weight of the dentifrice composition.

Surfactants

The compositions also may comprise surfactants, also commonly referred to as sudsing agents. Suitable surfactants are those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed in U.S. Pat. No. 3,959,458.

Nonionic surfactants that can be used in the compositions can broadly be defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from 8 to 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed in U.S. Pat. No. 4,051,234. The present composition typically comprises one or more surfactants each at a level of from 0.25% to 12%, preferably from 0.5% to 8%, and most preferably from 1% to 6%, by weight of the composition.

In an embodiment, the oral care composition includes a surfactant system comprising sodium laurel sulfate (SLS), cocamidopropyl betaine, or a mixture thereof.

Antimicrobial Agents

The present compositions may also include antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The water soluble antimicrobials include quaternary ammonium salts and bis-biquanide salts, among others. Triclosan monophosphate is a preferred additional water soluble antimicrobial agent. The quaternary ammonium agents include those in which one or two of the substitutes on the quaternary nitrogen has a carbon chain length (typically alkyl group) from 8 to 20, typically from 10 to 18 carbon atoms while the remaining substitutes (typically alkyl or benzyl group) have a lower number of carbon atoms, such as from 1 to 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethylhexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, issued Jun. 3, 1980, to Bailey.

Other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725 and in U.S. Pat. No. 4,051,234. Specific antimicrobial agents include chlorhexidine, triclosan, triclosan monophosphate, and flavor oils such as thymol. Triclosan is a preferred antimicrobial agent for inclusion in the present compositions. Triclosan and other agents of this type are disclosed in U.S. Pat. No. 5,015,466 and U.S. Pat. No. 4,894,220. These agents may be present at levels of from 0.01% to 1.5%, by weight of the composition.

Titanium dioxide may also be added to the present composition. Titanium dioxide is a white powder which adds opacity to the compositions. Titanium dioxide generally comprises from 0.25% to 5%, by weight of the composition.

Coloring agents may also be added to the present composition. The coloring agent may be in the form of an aqueous solution, preferably 1% coloring agent in a solution of water. Color solutions generally comprise from 0.01% to 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from 0.001% to 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from 0.005% to 5%, by weight of the composition.

A herbal agent, including but not limited to, golden thread extract, honeysuckle extract, and mixtures thereof, may also be present in the compositions herein at levels of from 0.01% to 0.05%. Such herbal agents are believed to provide anti-bacterial efficacy. Polyphenols may further be included at levels from 0.01% to 2%. A preferred polyphenol is tea polyphenol.

An effective amount of a desensitizing agent may also be incorporated into the present compositions. The desensitizing agents include those selected from alkaline metal salts with a chloride, nitrate sulfate, or acetate of a group II metal or aluminum or polymerizable monomer to occlude the tubules, alkaline metal or ammonium nitrate, ammonium oxylate, citric acid and sodium citrate. Preferred salts are potassium nitrate, potassium citrate, and mixtures thereof. Such desensitizing agents are disclosed in e.g., U.S. Pat. No. 5,718,885.

A stain reducing agent such as Plasdone S-630 or aluminum hydrate may further be added to the composition. Plasdone is polyvinyl pyrrolidone (PVP) that can be synthesized by polymerizing vinylpyrrolidone. Commercially, it has been produced as a series of products having mean molecular weights ranging from 10,000 to 700,000. Herein, the low molecular weights and middle molecular weights (from 10,000 to 100,000) are preferred. In order to remove stain effectively, the level of PVP is preferably from 0.5% to 10%, more preferably from 1.0% to 7.0%, and even more preferably from 1.5% to 5.0%.

The compositions of the present invention optionally comprise a nutrient. Suitable nutrients include vitamins, minerals, amino acids such as L-arginine, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

It is understood that while general attributes of each of the above categories of materials may differ, there may be some common attributes and any given material may serve multiple purposes within two or more of such categories of materials. All of the ingredients in the compositions may have functions in addition to their primary function, and may contribute to the overall properties of the composition, including its stability, efficacy, consistency, mouthfeel, taste, odor and so forth. Preferably, the carrier ingredients are selected for compatibility with other ingredients of the composition.

A type of product form of the present invention is a dentifrice. The term "dentifrice" generally denotes formulations which are used to clean the surfaces of the oral cavity. The dentifrice is an oral composition that is not intentionally swallowed for purposes of systemic administration of therapeutic agents, but is applied to the oral cavity, used to treat the oral cavity and then expectorated. Typically the dentifrice is used in conjunction with a cleaning implement such as a toothbrush, usually by applying it to the bristles of the toothbrush and then brushing the accessible surfaces of the oral cavity. Preferably the dentifrice is in the form of a paste or a gel (or a combination thereof)

The oral care compositions of the invention are typically in a single phase. However, in some embodiments, components are physically separated, for example by using a dual compartmented package. The dentifrice compositions may be a paste, gel, or any configuration or combination thereof. A further embodiment of the present invention includes dual-phase or multi-phase compositions comprising the present low-water compositions as one phase and at least one other separate phase comprising additional dentifrice components to further enhance stability, performance and/or aesthetics of the dentifrice product. For example, a dual phase composition may comprise a first phase comprising the present low-water composition with polyphosphate and ionic active(s) and a separate second phase comprising additional active agents such as bleaching agents, preferably a peroxide source, or a tooth surface conditioning agent to provide improved cleaning, whitening, anti-staining and mouth feel benefits. Examples of tooth conditioning agents are polysiloxanes and modified polysiloxanes, including diorganopolysiloxanes such as polydimethylsiloxane (PDMS); alkyl- and alkoxy-dimethicone copolyols such as $C_{12}$ to $C_{20}$ alkyl dimethicone copolyols; and aminoalkylsilicones. These siloxane polymers are described for example in U.S. Pat. Nos. 5,759,523; 6,024,891; 6,123,950; 6,019,962; and 6,139,823.

The dispenser for the dentifrice compositions may be a tube, pump, or any other container suitable for dispensing toothpaste. In a dual phase oral composition, each oral composition will be contained in a physically separated compartment of a dispenser and dispensed side-by-side.

Methods of Use

In practicing the embodiments, the user need only apply the oral care composition herein, to the tooth surfaces of a human or animal, in the areas desired, in order to obtain a desired effect, e.g., plaque reduction or prevention, whitening, breath freshening, caries prevention, pain relief, gum health, tartar control, erosion control, etc. Use of dentifrices to control erosion of the tooth surface, or to prevent demineralization, are known and described in, for example, U.S. Pat. No. 6,685,920. The compositions also may be applied to other oral cavity surfaces, such as the gingival or mucosal tissues, although it is believed that the benefits are best achieved when the dentifrice compositions are applied to the teeth. The dentifrice composition may contact the tooth and/or oral cavity surface either directly, or indirectly, however, it is preferred that the dentifrice composition be directly applied. The dentifrice composition may be applied by any means, but is preferably applied with a brush or by rinsing with a dentifrice slurry. The application may be at least once a day, although up to five times per day may be preferred, and may be carried out over a duration of time, e.g., one week, up to one year, up to three years or for a lifetime The manufacture of the oral composition of the present invention may be accomplished by any of the various standard techniques for producing such compositions. For example, preparation methods for dentifrices are well known, for example, as described in U.S. Pat. No. 3,966,863; U.S. Pat. No. 3,980,767; U.S. Pat. No. 4,328,205; and U.S. Pat. No. 4,358,437. To make a dentifrice, a vehicle may be prepared containing humectant, for example, one or more of glycerin, glycerol, sorbitol, and propylene glycol, thickener agents and antibacterial agent such as triclosan, and the vehicle and a mixture of anionic and amphoteric surfactants are added, followed by blending in of a polishing agent, as well as fluoride salts, with the pre-mix. Finally, flavoring agent, is admixed and the pH is adjusted to between 6.8 to 7.0.

Some embodiments of the present invention provide an oral care composition (Composition 1) comprising:
(a) an orally acceptable carrier;
(b) a source of fluoride ions;
(c) a source of stannous ions;
(d) an insoluble source of zinc ions;
(e) a buffering system comprising citric acid wherein the amount of citric acid is at least 1% by weight of the composition, and
wherein the composition has a total water content of less than 15% by weight, for example:
1.1. Composition 1 wherein the amount of citric acid is 0.5-4 wt. % or 1-3 wt. %, or 1.1-1.5 wt. % or 1.8-2.2 wt. % or 1.3% or 2% by weight.
1.2. Any of the foregoing compositions wherein the insoluble source of zinc ions comprises a zinc salt of an organic acid;
1.3. Any of the foregoing compositions wherein the insoluble source of zinc ions comprises zinc oxide, zinc phosphate, zinc pyrophosphate or a mixture thereof;
1.4. Any of the foregoing compositions wherein the fluoride ion source is a salt selected from stannous fluoride, sodium fluoride, potassium fluoride, sodium monofluorophosphate, sodium fluorosilicate, ammonium fluorosilicate, amine fluoride (e.g., N'-octadecyl-trimethylendiamine-N,N,N'-tris(2-ethanol)-dihydrofluoride), ammonium fluoride, titanium fluoride, hexafluorosulfate, and combinations thereof;
1.5. Any of the foregoing compositions wherein the stannous ion source is selected from stannous fluoride, stannous chloride dehydrate, stannous acetate, stannous tartrate, sodium stannous citrate, or a mixture thereof;
1.6. Any of the foregoing compositions wherein the source of fluoride ions and the source of stannous ions comprises stannous fluoride;
1.7. Any of the foregoing compositions comprising at least one polyphosphate salt selected from the group consisting of inorganic polyphosphate salts which have equal to or less than three phosphorous atoms
1.8. Composition 1.5 wherein the at least one polyphosphate is selected from the group consisting of tetrasodium pyrophosphate, sodium tripolyphosphate, and mixtures thereof; wherein the total polyphosphate comprises from 1 to 10 wt % of the composition;
1.9. Any of the foregoing compositions wherein the buffering system comprises a mixture of citric acid and trisodium citrate;
1.10. Any of the foregoing compositions comprising a thickening agent which comprises, in combination, cross-linked polyvinylpyrrolidone and a gum;
1.11. Any of the foregoing compositions comprising a thickening agent which comprises a cellulose, a synthetic block copolymer of ethylene oxide and propylene oxide, or a mixture thereof;
1.12. Any of the foregoing compositions wherein the zinc ion source is present in an amount of from 0.1 to 2 wt. %, or from 0.5% to 1.5 wt. % or from 0.9% to 1.1 wt. %;
1.13. Any of the foregoing compositions wherein the stannous ion source is present in an amount of from 0.05% to 5% wt., or from 0.1% to 1% wt.; or from 0.35-0.55 wt. %
1.14. Any of the foregoing compositions wherein the amount fluoride ion source is from 0.1% to 5%, or from 0.2% to 1%, or from 0.3 to 0.6%, by weight of the total composition;
1.15. Any of the foregoing compositions wherein the composition has a total water content of less than 20%, or less than 15%, or from less than 15% to greater than 10 wt. %, based on the weight of the composition;
1.16. Any of the foregoing compositions wherein combined metal ion source is present in an amount of from 0.15% to 7%, by weight, or from 0.6 to 2.5%, or from 1.25% to 1.65%, by weight of the composition;
1.17. Any of the foregoing compositions comprising a methyl vinyl ether/maleic anhydride copolymer having an average molecular weight (M.W.) of 30,000 to 1,000,000, e.g. 300,000 to 800,000;
1.18. Any of the foregoing compositions comprising L-arginine in free or orally acceptable salt form;
1.19. Any of the foregoing compositions comprising additional buffering agents, e.g., sodium phosphate buffer (e.g., sodium phosphate monobasic and disodium phosphate);
1.20. Any of the foregoing compositions comprising a humectant, e.g., selected from, sorbitol, propylene glycol, polyethylene glycol, xylitol, and mixtures thereof;
1.21. Any of the foregoing compositions further comprising an abrasive or particulate;
1.22. The foregoing composition wherein the abrasive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof;

1.23. Any of the foregoing compositions comprising an abrasive in an amount of 15 wt. % to 70 wt. % of the total composition weight;

1.24. Any of the foregoing compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from 0.3% to 4.5% by weight;

1.25. Any of the foregoing compositions further comprising one or more polymers selected from polyethylene glycols, polysaccharides (e.g., cellulose derivatives, for example carboxymethyl cellulose, polysaccharide gums, for example xanthan gum or carrageenan gum), and combinations thereof;

1.26. Any of the foregoing compositions comprising one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride;

1.27. Any of the foregoing compositions comprising a whitening agent, e.g., a selected from the group consisting of peroxides, metal chlorites, perborates, percarbonates, peroxyacids, hypochlorites, and combinations thereof;

1.28. Any of the foregoing compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.29. Any of the foregoing compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate;

1.30. Any of the foregoing compositions further comprising a soluble calcium salt, e.g., selected from calcium sulfate, calcium chloride, calcium nitrate, calcium acetate, calcium lactate, and combinations thereof;

1.31. Any of the foregoing compositions further comprising a physiologically or orally acceptable potassium salt, e.g., potassium nitrate or potassium chloride, in an amount effective to reduce dentinal sensitivity;

1.32. Any of the foregoing compositions in the form of a dentifrice, for example a toothpaste, e.g., a clear gel or opaque toothpaste;

1.33. Any of the foregoing compositions in the form of a single phase;

1.34. Any of the foregoing compositions comprising one or more of the following in the recited amounts:

| | |
|---|---|
| Citric acid | 0.5-3 or 1.1-1.5 or 1.8-2.2 wt. % |
| Trisodium citrate | 0.5-10 or 1-6 or 2-4 or 2.9-3.1 wt % |
| Zinc oxide | 0.1-5 or 0.5-2 or 0.9-1.1 wt % |
| Stannous fluoride | 0.1-5, or 0.1-2, or 0.4-0.6% wt % |
| Glycerin | 10-50 wt % |
| Propylene glycol | 1-25, or 2-10, or 6-8 wt % |
| Xantham gum | 0.1-12 or 0.1-1, or 0.1-.0.5 or 0.275-0.325 wt % |
| polyvinylpyrrolidone | 0.25-10 wt % |
| CMC | 0.2-1.5 or 0.3-0.9 or 0.65-0.75% |
| Silica (total) | 5-60 or 10-50, or 10-40 or 22-26 wt % |
| Tetrasodium Pyrophosphate (TSPP) | 0.1-10 or 0.5-5 or 1-4 or 1.75-2.25 wt % |
| Sodium acid pyrophosphate (SAPP) | 0-5 or 0-3 or 0.5-1.5 or 0.9-1.1 wt % |
| Sodium Tripolyphosphate (STPP) | 0.1-10, or 0.5-5 or 1-4, or 2.75-3.25 wt % |
| Sodium lauryl sulfate (SLS) | 0.1-10, or 0.2-5, or 1.2-2.5 or 1.5-1.75 wt % |
| Cocamidopropyl betaine | 0.1-10, or 0.5-5 or 0.5-2 or 0.75 to 1.25 wt % |

1.35. Any of the foregoing compositions which does not contain methylvinyl ether-maleic anhydride copolymer;

1.36. A method of treating or preventing a disease or condition of the oral cavity comprising contacting an oral cavity surface of a patient in need thereof with the composition of any one of the foregoing compositions;

1.37. Any of the foregoing methods which is a method for the treatment and prevention of bacterial plaque accumulation or prevention of tooth erosion.

The following examples are further illustrative of the preferred embodiments, but it is understood that the invention is not limited thereto.

EXAMPLES

Example 1

Procedure

Four formulations are prepared with the ingredients indicated for Formula A, with the amounts of CMC and citric acid, TKPP, SAPP and STPP varied as indicated in Tables 1 and 2.

The technique to determine water soluble tin and water soluble zinc in the formulations is by flame atomic absorption spectroscopy (FAAS). A suitable double beam atomic absorption spectrophotometer fitted with an air-acetylene burner and deuterium background correction, e.g. Varian SpectrAA 220FS, can be used. Also, a suitable zinc hollow cathode lamp and AA grade acetylene can be used. Water soluble zinc or tin can be measured in the compositions by FAAS after dilution of a sample in water and comparing to zinc or tin standards. A portion of the formulation is dispersed with water, solutions are transferred to a volumetric flask, diluted to volume with water and centrifuged. Tin or zinc is detected in the supernatant by atomic absorption spectroscopy and quantitated by comparing the absorbance of the sample solution to absorbances of external calibration standards of known tin or zinc concentration. To determine total tin or zinc, rather than dispersing the samples in water, the samples are digested with a suitable acid mixture, e.g., hydrochloric, nitric, and or hydrofluoric, over a steam bath.

The formulas are aged at 40° C. for up to 13 weeks. The total tin, total zinc, soluble tin and soluble zinc levels are determined at various time points.

TABLE 1

| Product | Test | Initial | 4 wk | 8 wk | 13 wk |
|---|---|---|---|---|---|
| 0% CMC + 1.3% Citric Acid | Soluble Tin | 0.25 | 0.12 | 0.09 | 0.17 |
| | Soluble Zinc | 0.69 | 0.68 | 0.57 | 0.55 |
| | Total Tin | 0.35 | — | — | — |
| | Total Zinc | 0.96 | — | — | — |
| | pH (as is) | 5.73 | 6.53 | 6.56 | 6.61 |
| | 10% pH | 7.96 | 8.05 | 7.88 | 7.89 |
| 0.4% CMC + 1.3% Citric Acid | Soluble Tin | 0.25 | 0.12 | 0.1 | 0.11 |
| | Soluble Zinc | 0.68 | 0.66 | 0.59 | 0.625 |
| | Total Tin | 0.35 | — | — | — |
| | Total Zinc | 0.92 | — | — | — |
| | pH (as is) | 6.1 | 6.89 | 6.78 | 6.93 |
| | 10% pH | 8.02 | 7.77 | 7.77 | 7.65 |
| 0% CMC + 2% Citric Acid | Soluble Tin | 0.33 | 0.28 | 0.29 | 0.34 |
| | Soluble Zinc | 0.64 | 0.7 | 0.62 | 0.6 |
| | Total Tin | 0.34 | — | — | — |
| | Total Zinc | 0.72 | — | — | — |
| | pH (as is) | 5.32 | 5.9 | 5.96 | 5.98 |
| | 10% pH | 6.77 | 6.83 | 6.81 | 6.84 |
| 0.4% CMC + 2% Citric Acid | Soluble Tin | 0.35 | 0.33 | 0.35 | 0.32 |
| | Soluble Zinc | 0.62 | 0.63 | 0.54 | 0.63 |
| | Total Tin | 0.37 | — | — | — |
| | Total Zinc | 0.76 | — | — | — |
| | pH (as is) | 5.9 | 6.07 | 6.11 | 6.13 |
| | 10% pH | 6.67 | 6.75 | 6.74 | 6.67 |

TABLE 2

| | Percent Zinc Soluble | | | |
|---|---|---|---|---|
| | Initial | 4 wk | 8 wk | 13 wk |
| Sn + ZnO + 1.3% Citric Acid + 0% CMC | 71.88% | 70.83% | 59.38% | 57.29% |
| Sn + ZnO + 1.3% Citric Acid + 0.4% CMC | 73.91% | 71.74% | 64.13% | 67.93% |
| Sn + ZnO + 2.0% Citric Acid + 0% CMC | 88.89% | 97.22% | 86.11% | 83.33% |
| Sn + ZnO + 2.0% Citric Acid + 0.4% CMC | 81.58% | 82.89% | 71.05% | 82.89% |

Formula A

| Ingredient | Weight % |
|---|---|
| Demineralized Water | 10 |
| Sodium Saccharin | 0.6 |
| Trisodium Citrate Dihydrate | 3 |
| Citric Acid-Anydrous | 1.3-2 |
| Stannous Fluoride | 0.45 |
| Zinc Oxide | 1 |
| Tetrasodium Pyrophosphate | 0-2 |
| Sodium Tripolyphosphate | 0-3 |
| 99.0%-101.0% Glycerin | balance |
| Polyethylene Glycol 600 | 3 |
| Propylene Glycol | 4 |
| PVP | 1 |
| Dye | <0.01 |
| Titanium Dioxide Coated Mica | 0.15 |
| Xanthan Gum | 0.3 |
| Carboxymethyl Cellulose (CMC 7) | 0-0.4 |
| Syn. Amorph. PPT. Silica-Abrasive | 12 |

TABLE 2-continued

| High Cleaning Silica | 12 |
|---|---|
| Sodium Lauryl Sulfate Powder | 1.75 |
| Cocamidopropyl Betaine | 1 |
| Flavor | 1.4 |
| Total | 100 |

Solubility of Stannous Fluoride: 31 g/100 mL (0° C.), 35 g/100 mL (20° C.)

Results

Comparative Example

Earlier work with a formula comprising a soluble zinc source (2 wt. % zinc citrate) and 0.454 wt. % stannous fluoride with 0.6 wt. % citric acid/3.0 wt. % trisodium citrate. This formula had an initial amount of soluble zinc of only 0.39 wt. % which decreased slightly to 0.34 wt. % after 12 weeks of aging. The amount of stannous remained steady from its initial solubility to the end of the 12 week aging period (ranging from 0.31 wt. %-0.36 wt. %).

Surprisingly, formulas with or without CMC with the same amount (0.454 wt. %) stannous fluoride and a lesser amount (1 wt. %) of less soluble zinc source (ZnO) showed greater initial solubility when greater than 1 wt. % citric acid was used (ranging from 0.62 wt. % to 0.69 wt. %) and this higher level of solubility was maintained despite 13 weeks of aging (0.55 wt. % to 0.63 wt. %).

Furthermore, when the amount of citric acid was increased to 2%, the initial amount of soluble stannous and amount after 13 weeks of aging (0.32 wt. % to 0.35 wt. %) was comparable to the ranges measured in the Comparative Example.

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising in a single phase:
   (a) an orally acceptable vehicle;
   (b) a source of fluoride ions;
   (c) a source of stannous ions;
   (d) an insoluble source of zinc ions;
   (e) a buffering system comprising citric acid wherein the amount of citric acid is at least 1% by weight of the composition, and
   wherein the composition has a total water content of less than 15% by weight, based on the weight of the composition.

2. The composition of claim 1 wherein the amount of citric acid is 1-3 wt. %, or 1.1-1.5 wt. % or 1.8-2.2 wt. %, based on the weight of the composition.

3. The composition of claim 1 wherein the amount of citric acid is 1-3 wt. % based on the weight of the composition.

4. The composition of claim 1 wherein the amount of citric acid is 1.1-1.5 wt. % based on the weight of the composition.

5. The composition of claim 1 wherein the amount of citric acid is 1.8-2.2 wt. % based on the weight of the composition.

6. The composition of claim 1, wherein the insoluble source of zinc ions comprises zinc oxide, zinc phosphate, zinc pyrophosphate or a mixture thereof.

7. The composition of claim 1 wherein the source of fluoride ions and the source of stannous ions comprises stannous fluoride.

8. The composition of claim 1 comprising at least one polyphosphate salt selected from the group consisting of inorganic polyphosphate salts which have equal to or less than three phosphorous atoms.

9. The composition of claim 8, wherein the at least one polyphosphate is selected from the group consisting of tetrasodium pyrophosphate, sodium tripolyphosphate, and mixtures thereof; wherein the total polyphosphate comprises from 1 to 10 wt % of the composition.

10. The composition of claim 1 wherein the buffering system comprises a mixture of citric acid and trisodium citrate.

11. The composition of claim 1 comprising polyvinylpyrrolidone, a gum, or a mixture thereof.

12. The composition of claim 1 comprising a modified cellulose such as carboxymethyl cellulose.

13. The composition of claim 1 further comprising at least one humectant selected from the group consisting of glycerin, polyethylene glycol, propylene glycol, and mixtures thereof.

14. The composition of claim 1 wherein the composition is a dentifrice comprising one or more of an abrasive, a surfactant, a foaming agent, a vitamin, a polymer, a whitening agent, an enzyme, a humectant, a thickener, an antimicrobial agent, a preservative, L-arginine, a flavoring, or a coloring agent.

15. The composition of claim 1 comprising:
(a) 1-3 wt. % citric acid;
(b) 0.5-10 wt % Trisodium citrate;
(c) 0.1-5 wt % Zinc oxide;
(d) 0.1-5 wt % Stannous fluoride;
(e) 10-50 wt % Glycerin;
(f) 1-25 wt. % Propylene glycol; optionally comprising one or more of:
(g) 0.1-12 wt % xanthan gum;
(h) 0.25-10 wt % polyvinylpyrrolidone (PVP);
(i) 0.2-1.5% wt. % carboxymethylcellulose (CMC);
(j) 5-60 wt % Silica (total);
(k) 0.1-10 wt % Tetrasodium Pyrophosphate (TSPP);
(l) 0-5 wt % Sodium acid pyrophosphate (SAPP);
(m) 0.1-10 wt % Sodium Tripolyphosphate (STPP);
(n) 0.1-10 wt % Sodium lauryl sulfate (SLS);
(o) 0.1-10 wt % Cocamidopropyl betaine.

16. The oral care composition of claim 15 comprising:
(a) 1.1-1.5 wt. % or 1.8-2.2 wt. % citric acid;
(b) 2-4 wt % Trisodium citrate;
(c) 0.5-2 wt % Zinc oxide;
(d) 0.1-2 wt % Stannous fluoride;
(e) 10-50 wt % Glycerin;
(f) 2-10 wt % Propylene glycol; optionally comprising one or more of:
(g) 0.1-0.5% wt % xanthan gum;
(h) 0.25-10 wt % polyvinylpyrrolidone (PVP);
(i) 0.3-0.9 wt. % carboxymethylcellulose (CMC);
(j) 10-40 wt % Silica (total);
(k) 1-4 wt % Tetrasodium Pyrophosphate (TSPP);
(l) 0.5-1.5 wt % Sodium acid pyrophosphate (SAPP);
(m) 1-4 wt % Sodium Tripolyphosphate (STPP);
(n) 1.2-2.5 wt % Sodium lauryl sulfate (SLS);
(o) 0.5-2 wt % Cocamidopropyl betaine.

17. The oral care composition of claim 16 comprising:
(a) 1.1-1.5 wt. % or 1.8-2.2 wt. % citric acid;
(b) 2.9-3.1 wt % Trisodium citrate;
(c) 0.9-1.1 wt % Zinc oxide;
(d) 0.4-0.6% wt % Stannous fluoride;
(e) 10-50 wt % Glycerin;
(f) 6-8 wt % Propylene glycol; optionally comprising one or more of:
(g) 0.275-0.325 wt % xanthan gum;
(h) 0.25-10 wt % polyvinylpyrrolidone (PVP);
(i) 0.65-0.75 wt. % carboxymethylcellulose (CMC);
(j) 22-26 wt % Silica (total);
(k) 1.75-2.25 wt % Tetrasodium Pyrophosphate (TSPP);
(l) 0.9-1.1 wt % Sodium acid pyrophosphate (SAPP);
(m) 2.75-3.25 wt % Sodium Tripolyphosphate (STPP);
(n) 1.5-1.75 wt % Sodium lauryl sulfate (SLS);
(o) 0.75 to 1.25 wt % Cocamidopropyl betaine.

18. A method of treating a disease or condition of the oral cavity comprising contacting an oral cavity surface of a patient in need thereof with the composition of claim 1.

19. The method of claim 18, wherein the disease or condition of the oral cavity is biofilm formation, plaque formation, oral inflammation or a combination thereof.

* * * * *